US008900634B2

(12) United States Patent
Ryoo et al.

(10) Patent No.: US 8,900,634 B2
(45) Date of Patent: Dec. 2, 2014

(54) DIETHYLSTILBESTROL DOSAGE FORM AND METHODS OF TREATMENT USING THEREOF

(75) Inventors: Je Phil Ryoo, Princeton, NJ (US); Chun Kwong Chu, Shatin (HK); Zheng Wang, Bridgewater, NJ (US); Diana Shu-Lian Chow, Houston, TX (US); Roland A. Ako, Houston, TX (US)

(73) Assignee: NAL Pharmaceuticals, Ltd., Causeway Bay (HK)

( * ) Notice: Subject to any disclaimer, the term of this patent is extended or adjusted under 35 U.S.C. 154(b) by 280 days.

(21) Appl. No.: 13/040,143

(22) Filed: Mar. 3, 2011

(65) Prior Publication Data

US 2011/0189288 A1 Aug. 4, 2011

Related U.S. Application Data

(63) Continuation-in-part of application No. 12/608,445, filed on Oct. 29, 2009, now Pat. No. 8,715,715.

(60) Provisional application No. 61/110,775, filed on Nov. 3, 2008.

(51) Int. Cl.
| A61K 9/70 | (2006.01) |
| A61K 31/56 | (2006.01) |
| A61K 31/05 | (2006.01) |
| A61K 9/00 | (2006.01) |

(52) U.S. Cl.
CPC ............ *A61K 31/05* (2013.01); *A61K 9/7007* (2013.01); *A61K 31/56* (2013.01); *A61K 9/006* (2013.01)
USPC ...................................... 424/484

(58) Field of Classification Search
None
See application file for complete search history.

(56) References Cited

U.S. PATENT DOCUMENTS

| 8,105,625 B2 * | 1/2012 | Rajewski et al. ............ 424/452 |
| 2002/0015730 A1 * | 2/2002 | Hoffmann et al. ............ 424/470 |
| 2003/0180352 A1 | 9/2003 | Patel et al. |
| 2010/0112050 A1 | 5/2010 | Ryoo et al. |

FOREIGN PATENT DOCUMENTS

| WO | 2007125533 A2 | 11/2007 |
| WO | WO 2007125533 A2 * | 11/2007 |
| WO | 2009029543 A1 | 3/2009 |

OTHER PUBLICATIONS

Mitsubishi-Kagaku Foods Corporation, "Introduction of Sugar Esters," http://www.mfc.co.jp/english/whatsse.htm, Oct. 12, 2009, total 4 pages.*
Carter et al. (Diethylstilbestrol: Recommended dosages for different categories of Breast Cancer Patients), May 9, 1977, JAMA 237:2079-2085.*
Mitsubishi-Kagaku Foods Corporation, Introduction of Sugar Esters, HTTP www.mfc.co.jp/english/whatsse.htm. Oct. 12, 2009, total 4 pages.*

(Continued)

*Primary Examiner* — Anand Desai
*Assistant Examiner* — Melissa Mercier
(74) *Attorney, Agent, or Firm* — Lucas & Mercanti, LLP

(57) ABSTRACT

Oral dosage forms as a biodegradable, water soluble film for delivering pharmaceutically active agents, particularly diethylstilbestrol and pharmaceutically acceptable salts thereof to patients through insertion into the mouth of patient and methods for administering pharmaceutically active agents to patients by insertion into the mouth to provide selective uptake of said agents through the mucosa and thus avoiding the gastrointestinal tract.

17 Claims, 3 Drawing Sheets

(56) References Cited

OTHER PUBLICATIONS

Carter et al. Diethylstilbestrol: Recommended dosage for different categories of Breast Cancer Patients, May 9, 1977, JAMA 237:2079-2085.*

Okamoto, Hirokazu et al., "Effect of Sucrose Fatty Acid Esters on Transdermal Permeation of Lidocaine and Ketoprofen", Article, Biol. Pharm. Bull. 28(9) 1689-1694 (2005).

International Search Report of PCT/US2009/062776 dated Feb. 23, 2012.

Szuts, et al., Study of Thermo-Sensitive Gel-Forming Properties of Sucrose Stearates, Article, J. Excipients and Food Chem. 1(2) 2010 pp. 13-20.

International Search Report of PCT/GB2012/050475 dated May 30, 2012.

Okamoto, Hirokazu et al., Effect of Sucrose Fatty Acid Esters on Transdermal Permeation of Lidocaine and Ketoprofen, Article, Biol. Pharm. Bull 28(9) pp. 1689-1694 (2005).

Femenia-Font, A., et al., Effect of Chemical Enhancers on the In Virto Percutaneous Absorption of Sumatriptan Succinate, Article, European Journal of Pharmaceutics and Biopharmaceutics 61 (2005) pp. 50-55.

Balaguer-Fernandez, et al., Sumatriptan Succinate Transdermal Dellivery Systems for the Treatment of Migraine, Article, Journal of Pharmaceutical Sciences, vol. 97, No. 6, Jun. 2008, pp. 2102-2109.

* cited by examiner

DIETHYLSTILBESTROL DOSAGE FORM AND METHODS OF TREATMENT USING THEREOF

CROSS REFERENCE TO RELATED APPLICATIONS

This application is a Continuation-in-Part of application Ser. No. 12/608,445, filed Oct. 29, 2009, now U.S. Pat. No. 8,715,715 which claims the benefit of Provisional Application Ser. No. 61/110,775 filed Nov. 3, 2008. Each of these applications is hereby incorporated herein by reference.

FIELD OF THE INVENTION

The present invention relates to oral dosage forms for insertion into the mouth for selective adsorption by the mucosal tissue, particularly for administration of medicinal agents where fast onset of action is desirable and hepatic first-pass effect is not desirable. In particular, the present invention relates to pharmaceutical formulation of the anti-prostate cancer and anti-breast cancer drug diethylstilbestrol.

BACKGROUND OF THE INVENTION

Prostate cancer is the second leading cause of new cancer cases in men worldwide and the six leading cause of cancer death in men. In the US, over two (2) million men currently suffer with prostate cancer and it is estimated that there were approximately 30,000 deaths due to the disease in 2008.

Diethylstilbestrol (DES) is a synthetic nonsteroidal estrogen (female sex hormone). It has been used in the treatment of both Androgen dependent and androgen-independent prostatic carcinoma. DES was the first effective drug for treatment of metastatic prostate cancer in 1941. It was first synthesized in London by Dodds in 1938. DES is inexpensive to manufacture however its biological properties are similar to those of naturally occurring expensive estrogens.

Oral diethylstilbestrol is an effective dosage form for the treatment of prostate cancer. It induces castrate serum testosterone levels. Studies have demonstrated that DES may improve the survival of patients with advanced prostate cancer compared with orchiectomy and luteinizing hormone-releasing hormone (LHRH). This is due to its positive effects on the bone by reducing osteoporosis and retarding the development of bond metastases. Oral DES therapy for prostate cancer is associated with excess cardiovascular side effects (heart attack, stroke and thrombosis). The cardiovascular side effects of DES are thought to be associated with DES metabolism in the liver. When estrogens are given orally, they are subject to intestinal and hepatic first-pass effect leading to high hormone concentrations in the liver promoting the synthesis of clotting proteins like fibrinogen.

Diethylstiltrol (DES) is effective in the treatment of both androgen dependent (ADPCa) and androgen-independent carcinoma (AIPCa). Oral DES therapy for prostate cancer is associated with excess cardiovascular side effects (heart attack, stroke and thrombosis). The cardiovascular side effects of DES are thought to be associated with DES metabolism in the liver. When estrogens are given orally, they are subject to intestinal and hepatic first-pass effect leading to high hormone concentrations in the liver promoting the synthesis of clotting proteins like fibrinogen.

US patent publication 2010/0016445 to Beer discloses methods for treating prostate cancer comprising transdermally administering a therapeutically effective amount of diethylstilbesterol (DES), or a pharmaceutically acceptable salt or complex thereof, to a subject. US patent publication 2003/0147936 discloses methods and products for the primary hormonal treatment of early stage, low and intermediate risk prostate cancers by prostatic implants of androgen suppressive drugs formulated as fused with a lipoid carrier or encapsulated in microcapsules or in Silastic capsules is provided. Such prostatic implants renders a constant slow-release of their contents to the prostate for extended periods by biodegradation and diffusion. These methods are designed to deliver long term low levels of DES. The present dosage form and method of treatment delivers high therapeutic levels DES quickly while avoiding the detrimental side effects.

Diethylstiltrol (DES) is effective in the treatment of both androgen dependent (ADPCa) and androgen-independent carcinoma (AIPCa).

SUMMARY OF INVENTION

We have discovered a water soluble matrix which can be incorporated into a solid, film or liquid oral dosage form for insertion into the mouth as a means for effectively delivering to, and transporting pharmaceutical active agents selectively through the oral mucosal tissue into the patient. This water soluble matrix system delivers the pharmaceutical active agent effectively and rapidly into the body through the mucous membranes in the mouth. This system is ideally suited for delivering DES.

Many prostate cancers need supplies of the male hormone testosterone to grow. Testosterone is produced by the testes and the adrenal glands. Stilboestrol reduces the level of testosterone in the body. It does this by making the brain think there are too many sex hormones circulating in the body. When this occurs, production of testosterone is 'switched off'. This reduced level of testosterone can help to slow down the growth of the cancer cells and may cause the cancer to shrink in size.

Oral DES therapy for prostate cancer is associated with excess cardiovascular side effects (heart attack, stroke and thrombosis). The cardiovascular side effects of DES are thought to be associated with DES metabolism in the liver. When estrogens are given orally, they are subject to intestinal and hepatic first-pass effect leading to high hormone concentrations in the liver promoting the synthesis of clotting proteins like fibrinogen.

Fibrinogen is a 340-kD glycoprotein that is synthesized in the liver and helps stop bleeding by forming blood clots to plug the bleeding area. It circulates in plasma at a concentration of 2-4 g/L, with a half-life of 4 days. The primary physiological role of fibrinogen is in blood coagulation. In the final step of the coagulation cascade, fibrinogen is converted to fibrin by thrombin to form a fibrin clot. The first step in this conversion is the cleavage of fibrinopeptides A and B from the fibrinogen $\alpha$ and $\beta$ chains by thrombin. The residual molecule formed is referred to as a fibrin monomer. A loose fibrin clot develops as fibrin monomers spontaneously polymerize. The formation of a firm insoluble fibrin gel depends on cross-linking of the polymer by the transglutaminase activity of factor XIIIa (another clotting factor). In some patients with low coagulation-to-fibrinolysis balance, higher than normal levels of fibrinogen can promote the formation of clots in the absence of active bleeding.

Recognition of the cardiovascular side effects has led to the development of formulations and routes of delivering DES that will bypass liver metabolism. In one embodiment, the delivery of DES is through the buccal route using an oral dissolving film of DES (ODF-DES). The buccal route bypasses the liver and potentially decreases the DES cardiovascular side effects and increase bioavailability.

The oral dosage matrix of this invention transports these pharmaceutically active agents selectively through the mucous membrane in the mouth bypassing the GI system so as to avoid GI irritations and deactivation of the active agent in the GI track. Without GI inactivation, less active agent is needed to produce a therapeutic result. In addition, the oral dosage matrix of this invention rapidly releases the pharmaceutically active agent for transport quickly into the blood stream of the patient. Transport of the active agents selectively through the mucus membranes of the mouth is facilitated by incorporating one or more fatty acid esters of sucrose having a combined hydrophilic lipophilic balance (HLB) of about 8 to about 16 with the active agent to form the matrix. The fatty acid esters of sucrose are an effective absorption enhancer. The oral dosage matrix of this invention produces improved bioavailability and delivery of the pharmaceutical active agent DES with rapid onset of therapeutic effectiveness for the patient.

The oral dosage matrix, pharmaceutically active agent and fatty acid ester of sucrose, may be added to additional ingredients to produce dosage forms such as a film, a rapid releasing solid such as a powder or granule, a tablet, and also a liquid which contain a therapeutically effective amount of the pharmaceutically active agent, DES. This oral dosage matrix when incorporated into a tablet, film or other solid dosage form or solid dosage unit may further comprise a polymeric mixture of polyvinyl pyrrolidone and a polymeric alginate. This solid dosage form is of a size suitable for insertion into the mouth.

DETAILED DESCRIPTION

Figure 1:
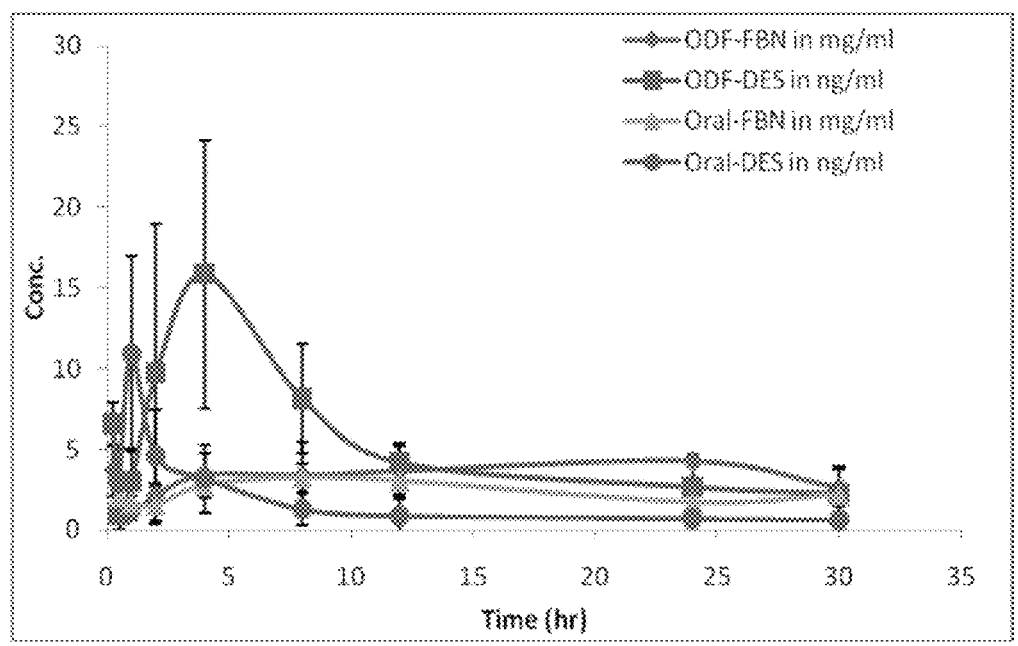
FIG. 1 is a graph of plasma concentrations of fibrinogen (FBN) and DES from Sprague-Dawley rats dosed with ODF and oral solution of DES (n=4).

In accordance with this invention, a new delivery matrix is provided for administering DES to a patient by means of selective absorption through mucous membranes located in the mouth. Absorption is the movement of drug into the blood stream. This invention constitutes a matrix which can be incorporated into new oral dosage forms such as a film or tablet and a liquid dosage form. The term oral dosage form shall include but not be limited to an oral disintegrating tablet, paste, gel, liquid, emulsion, film, lollipop, lozenge, buccal and gingival patch, granule and powdered dosage forms. The terms dosage form or dosage unit shall mean the combination of the matrix, which comprises a pharmaceutical active agent, DES, and one or more fatty acid esters of sucrose having a combined HLB of about 8 to about 16, preferably about 9 to about 16, with additional ingredients to form a tablet, paste, gel, liquid, emulsion, film, lollipop, lozenge, buccal and gingival patch, granule and powdered dosage form for insertion into the mouth of a patient. The dosage forms are preferably water soluble. The dosage form contains an effective amount of DES distributed therein. DES is practically insoluble in water and soluble in ethanol, chloroform, diethyl ether, acetone, dioxane, ethyl acetate, methyl alcohol, vegetable oils, and aqueous solutions of alkaline hydroxides. DES of the present invention may be in the from of a pharmaceutically acceptable salt of DES. Non-limiting examples of such salts would be mono and di sodium, mono and di potassium mono and di phosphate and monoglucuronide. The term pharmaceutical agent as used herein refers to DES and its pharmaceutically acceptable salts.

The dosage form may optionally contain a polymeric mixture of polyvinyl pyrrolidone and a polymeric alginate. When the dosage form is a solid it may be contoured to a size suitable for insertion into the mouth. Preferred solid dosage forms are a film (ODF) and a tablet (ODT). Insertion into the mouth preferably occurs by sublingual or buccal insertion which allows the pharmaceutical agent to be delivered to the patient selectively through the mucosa in the mouth thereby bypassing the GI system and allowing effective administration of DES without causing excess formation of fibrinogen and the related cardiovascular side effects such as heart attack, stroke and thrombosis.

In some instances, the dosage form is placed on to the tongue where absorption may also take place. The dosage forms of this invention act as a carrier device to transmit the DES to a patient in a fast and effective manner. Preferably, the liquid dosage form will be placed under the tongue for sublingual absorption. When only DES and fatty acid ester of sucrose are present in the liquid, then the liquid is the dosage form.

This invention also is directed to a process for treatment of both Androgen dependent and androgen-independent prostatic carcinoma. Diethylstilbestrol is also used for the treatment of breast cancer. In the treatment of breast cancer, from about 0.1 mg to about 15 mg per dose of DES is administered one to three times a day. In another embodiment from about 0.1 to about 0.5 mg per dose of DES is administered one to three times a day. In the treatment of prostate cancer, from about 0.1 mg to about 15 mg per dose of DES is administered one to three times a day. A preferred embodiment contains about 0.5 mg to about 15 mg administered one to three times a day. In another embodiment, the dose is about 0.1 mg to about 5 mg administered one to three times a day. DES may be DES or a pharmaceutically acceptable salt of DES.

By insertion of this dosage form into the mouth of the patient, the pharmaceutical agent is delivered by selective absorption through the patient's oral mucosa tissue. In another embodiment of the present invention, the dosage form is placed on the tongue. In another embodiment of the present invention, a liquid matrix is placed in the mouth of the patient and held there until the active agent has been absorbed. Absorption may take from about 0.5 minute to about 15 minutes preferably about 1 minute to about 10 minutes and more preferably 1 minute to about 5 minutes. Placing the liquid dosage form into the patient's mouth under the tongue is preferred. Liquid dosage forms may be applied by spraying into the mouth from suitable spray device or placed into the mouth with an eye dropper, pipette or similar device. Applicators are well known in the art. Dosing by film, tablet or liquid is preferably once or twice daily. Dosing may vary according to the age of the patient, severity of the condition and the particular active agent.

In one embodiment of the present invention the dosage form is a water soluble film comprising the matrix and a polymeric mixture of polyvinyl pyrrolidone and a polymeric alginate. Preferably the film contains from about 5% to about 95% by weight of polyvinyl pyrrolidone and from about 5% to about 95% of the polymeric alginate, both weights being based upon the weight of the film. This film is formed from an aqueous mixture containing from about 5% to about 95% by weight of polyvinyl pyrrolidone and from about 5% to about 95% of the alginate salt, both weights being based upon the dry weight of the mixture. The alginate salt can be any conventional pharmaceutically acceptable salt, preferably the alkali earth metal salts and more preferably sodium alginate. Both the polyvinyl pyrrolidone and a polymeric alginate utilized in forming this film are water soluble. Sufficient water is used in the formation of the aqueous mixture to dissolve the polyvinyl pyrrolidone and alginate salt.

The polyvinyl pyrrolidone which is utilized in forming the film has a molecular weight of from about $1 \times 10^3$ to about $1 \times 10^8$ daltons and the polymeric alginate has a molecular weight of from about $1 \times 10^3$ to about $1 \times 10^7$ daltons and a viscosity of from about 400 cps to about 900 cps measured in a 1% by weight aqueous solution.

The pharmaceutical composition of the present invention, further comprising a film forming agent selected from pullulan or a polymeric mixture of polyvinyl pyrrolidone and a polymeric alginate.

In a preferred embodiment of the present invention the dosage form is a water soluble film comprising the matrix and pullulan. Pullulan typically has a molecular weight of about 5,000 to about 5,000,000 daltons and preferably pullulan has a molecular weight of about 10,000 to about 800,000 daltons.

The film oral solid dosage unit has a surface area of from about 0.25 cm² to about 20 cm² and a weight of about 1 mg to about 200 mg, preferably from about 1 cm² to about 10 cm² and a weight of about 10 mg to about 500 mg, preferably about 10 mg to about 250 mg. The dry film has a thickness of between about 0.01 mm to about 5 mm, preferably between about 0.05 mm to about 2.5 mm. The film will dissolve in the oral cavity in about 0.25 minutes to about 15 minutes, preferably in about 0.5 minutes to about 10 minutes. When the pharmaceutical composition is a the tablet, when the placed in the oral cavity it will dissolve in about 0.25 minutes to about 15 minutes.

When the pharmaceutical composition is a film and said film preferably contains one or more absorption enhancers in an amount of from about 0.1% by weight to about 15% by weight of the film, more preferable, said film contains a absorption enhancer in an amount of from about 1% by weight to about 10% by weight of the film.

When the pharmaceutical composition is a tablet said tablet preferably contains a absorption enhancer in an amount of from about 0.1% by weight to about 20% by weight of the tablet, more preferably said tablet contains a absorption enhancer in an amount of from about 1% by weight to about 15% by weight of the tablet.

When the pharmaceutical composition is a liquid contains a absorption enhancer in an amount of from about 0.1% by weight to about 10% by weight of the liquid.

In controlled release oral solid dosage forms, films or tablets, the ratio of polyvinyl pyrrolidone to polymeric alginate in the polymeric mixture is from about 5:1 to about 1:3. By selecting different ratios of polyvinyl pyrrolidone to polymeric alginate, the dissolution time of the film may be controlled.

Additional polymers may be incorporated into the matrix as release controlling additives. Suitable additional polymers may be selected from the group comprising hydroxy propyl methyl cellulose, hydroxy ethyl cellulose, hydroxy propyl cellulose and polyethylene glycol and like polymers. Preferably, hydroxy ethylcellulose can be used to decrease film hydrophilicity and increase dissolution time to over 25 minutes for both buccal and sublingual applications. Hydroxy propyl methylcellulose can be also included to decrease film hydrophilicity and at the same time to decrease dissolution time to the range of 1-5 minutes.

The unit dosage form may contain known pharmaceutically acceptable additives, flavoring agents, surfactants, colorants, pigments, thickners and adjuvants. A non-limiting example of a pigment is titanium dioxide and non-limiting example of a thickener is sodium carboxymethylcellulose. Conventional plasticizers such as glycerol and sorbitol may also be present in amounts up to about 40%. Specifically examples of release-controlling additives such as hydroxypropyl methylcellulose, hydroxypropyl cellulose, and hydroxy ethyl cellulose can be added. Conventional flavors such as peppermint oil, sugar or other natural and artificial sweeteners and natural and artificial flavors may be present in the same form of composition of this invention. These additives, flavoring agents, sweeteners, plasticizers, surfactants and adjuvants may be incorporated into the film by adding to or mixing them into the aqueous solution which is used to form the film. Generally it is desired that these agents are present in the amount of from about 0.1% to about 20%. The controlled release matrix may contains one or more absorption enhancers present in an amount of from about 0.1% to about 20% based upon the weight of the dosage unit which may be a film or tablet preferably from about 1% to about 20%.

When the unit dosage form further comprises a nonionic surfactant, the combined nonionic surfactant and sucrose fatty acid ester have a combined HLB of about 8 to about 17.

The solid oral unit dosage form of this invention can be utilized to transport any desired pharmaceutically active agent. As used herein, the term "effective amount" designates the amount of drug or pharmaceutical agent that produces the desired biological or medical response of a patient. In accordance with this invention depending upon the pharmaceutical agent that is administered and the desired biological or medical response of a patient desired by the physician, the effective amount will vary. In general, the amount of a pharmaceutically active agent conventionally administered in other unit dosage forms can be used and administered by the unit dosage form of this invention. The dose of pharmaceutically active agent may be adjusted to take into account differences in absorption due to the different route of administration. The term "selective" as used herein is means that a major portion of the pharmaceutical agent administered passes through the mucosal membranes of the mouth rather than through the gastrointestinal tract.

The preferred pharmaceutical agent for use in the oral unit dosage form of this invention is DES. The amount which is presented in the dosage form of this invention should be that amount which is effective for treating prostate cancer and breast cancer.

The unit oral dosage of this invention contains a pharmaceutically acceptable mucosal penetrating or permeation enhancer. These pharmaceutically acceptable mucosal penetrating or permeation enhancers are incorporated into the film or tablet by adding to or mixing them into the solution which is used to form the film or tablet. These pharmaceutically acceptable mucosal penetrating or permeation enhancers are present in the total amount of about 0.5% to about 20%, preferably about 1% to about 20%, more preferably about 1% to about 10% and most preferably about 2% to about 10% based upon the weight of the dosage form. The preferred pharmaceutically acceptable mucosal penetrating or permeation enhancers are selected from the esters of sucrose particularly the C12 to C20 saturated fatty acid esters of sucrose. When one or more than one fatty acid ester of sucrose is included in the matrix, that is a film, oral disintegrating tablet, liquid, spray, paste, gel, oral film, lollipop, lozenge, buccal and gingival patch, the combined HLB of the fatty acid esters of sucrose will have an HLB of about 8 to about 16; preferably about 9 to about 16 and most preferably about 9.5 to about 16. The preferred fatty acid esters of sucrose are selected from the group consisting of sucrose stearate, sucrose palmitate, sucrose laurate, sucrose behenate, sucrose oleate and sucrose erucate. Table 2 lists the HLB values for fatty acid esters of sucrose and the monoester content.

TABLE 1

HLB Value of Fatty Acid Esters of Sucrose

| ESTER | Trade Name | HLB value | Mono ester content |
|---|---|---|---|
| Sucrose stearate | S-070 | <1 | <1% |
|  | S-170 | 1 | 1% |
|  | S-270 | 2 | 10% |
|  | S-370 | 3 | 20% |
|  | S-370 Fine | 3 | 20% |
|  | S-570 | 5 | 30% |
|  | S-770 | 7 | 40% |
|  | S-970 D-1809 | 9 | 50% |
|  | S-1170, D-1811 | 11 | 55% |
|  | S-1570 D-1815 | 15 | 70% |
|  | S-1670 D-1816 | 16 | 75% |
| Sucrose palmitate | p-170 | 1 | 1% |
|  | P-1570 D-1615 | 15 | 70% |
|  | P-1670 D-1616 | 16 | 80% |
| Sucrose laurate | L-195 | 1 | 1% |
|  | L-595 | 5 | 30% |
|  | LWA-1570 | 15 | 70% |
|  | L-1695 D-1216 | 16 | 80% |
| Sucrose behenate | B-370 | 3 | 20% |
| Sucrose oleate | O-170 | 1 | 1% |
|  | OWA-1570 | 15 | 70% |
| Sucrose erucate | ER-190 | 1 | 0% |
|  | ER-290 | 2 | 2% |
| Sucrose ester of mixed fatty acids | POS-135 | 1 | 0% |

The hydrophilic-lipophilic balance (HLB) of a surfactant is a measure of the degree to which it is hydrophilic or lipophilic, determined by calculating values for the different regions of the molecule, as described by W. C. Griffin "Classification of Surface-Active Agents by 'HLB,'" Journal of the Society of Cosmetic Chemists 1 (1949): 311. and W. C. Griffin "Calculation of HLB Values of Non-Ionic Surfactants," Journal of the Society of Cosmetic Chemists 5 (1954): 259. Other methods have been suggested, notably by J. T. Davies "A quantitative kinetic theory of emulsion type, I. Physical chemistry of the emulsifying agent," Gas/Liquid and Liquid/Liquid Interface. Proceedings of the International Congress of Surface Activity (1957): 426-438. All three references are incorporated herein by reference.

The HLB for a combination of components with differing HLB value is by the following formula:

$$HLB \text{ for a combination of components} = \frac{\sum_{i=1}^{n}(H_i \times A_i)}{\sum_{i=1}^{n}(A_i)}$$

where $H_i$ is the HLB value of individual component and $A_i$ is the amount of individual component.

The matrix of a preferred embodiment may further comprise a nonionic surfactant. Preferred nonionic surfactants may be one or more of a polysorbate, polyethylene glycol and sorbitan fatty acid ester.

The polysorbate useful in the present invention is selected from the group consisting of polyoxyethylene (20) sorbitan monolaurate, polyoxyethylene (20) sorbitan monopalmitate, polyoxyethylene (20) sorbitan and polyoxyethylene (20) sorbitan monooleate.

The sorbitan fatty acid ester useful in the present invention is selected from the group consisting of sorbitan monolaurate, sorbitan monopalmitate, sorbitan monostearate, sorbitan tristearate and sorbitan monooleate.

The matrix of this invention may further comprise a secondary absorption enhancer selected from the group consisting of glycerol, ginger oil, cineole and terpenes. Preferred terpines include limonene, cymene, pinene, pellandrene and the like.

The oral dosage form of the present invention may also contain taste masking agents. Taste masking agents may be for example sweeteners, flavors and blocking agents.

The oral unit dosage form of this invention is produced by forming an aqueous solution of the matrix and polyvinyl pyrrolidone and the polymeric alginate. In preparing the film, the aqueous solution containing polyvinyl pyrrolidone and sodium alginate is mixed with pharmaceutically active ingredient, plasticizers, surfactants and pharmaceutically acceptable additives, flavoring agents, adjuvants. This mixture is then cast into films by coating and drying generally using a coating and casting machine. Any conventional means of casting the films by means of these machines can be utilized in carrying out the procedure for forming the films. The aqueous mixture containing the polyvinyl pyrrolidone, sodium alginate, pharmaceutically active ingredient, plasticizers as well as certain desirable pharmaceutically acceptable additives, flavoring agents, adjuvants is coated on a release liner such as a polyester film. Any conventional release liner can be utilized for this purpose. Generally the release liner has a silicone surface to facilitate release of the film after drying. After the aqueous solution containing the polymeric mixture of polyvinyl pyrrolidone and alginate polymer is coated on the surface of the release liner, the coated release liner is heated to a temperature to dry the coated solution and allow the polyvinyl pyrrolidone and the alginate form a polymeric film with the pharmaceutically active agent dispersed therein, preferably uniformly dispersed therein. Generally drying can take place at from about 60° to 80° C. or higher depending on thickness of the film desired. Drying time can range from 10 minutes for 4 hours. The drying and formation of polyvinyl pyrrolidone and sodium alginate polymer films can be carried out by conventional means. Once the film is dried, the film is die-cut into standard sizes and removed from the release liner to produce the oral unit dosage form. Generally for the oral usage dosage in the form of the film has a surface area from about 0.25 cm² to about 20 cm² and a weight of about 1 mg to about 200 mg, preferably from about 1 cm² to about 10 cm² and a weight of about 10 mg to about 200 mg and a thickness of from about 0.1 mm to about 5 mm.

In preparing the orally disintegrating tablet, the fatty acid ester of sucrose is dissolved in a solvent such as isopropyl alcohol at elevated temperature of about 60° C. Certain adjuvants such as flavoring agents, and nonionic surfactants are added to the solution to form solution A. If to be included in the tablet release controlling agents such as polyvinyl pyrrolidone (PVP) and alginate salt is prepared by dissolving in water. Fillers and sweeteners such as mannitol and sucrose are blended to become a powder B. In a fluidized-bed granulator, powder B is sprayed with solution A and the optional PVP:alginate solution. The mixture is dried until completely dry. The mixture is then passed through a 20 mesh screen or similar process to produce a granulation. This granulated PVP is combined with pharmaceutically active agent, preferably a triptan and additional dry ingredients such as the additional polymers, sweetener, lubricant which have a particle size equivalent to being passed through a 60 mesh screen to form the final granulation for tableting. Tablets of appropriate size and shape are then prepared by techniques well know in the pharmaceutical arts. The formation of tablets that rapidly dissolve in the oral cavity is known in the art. Such tablets have, for example, been described in U.S. Pat. Nos. 7,431,942; 5,464,632; and 5,026,560 which are incorporated herein by reference.

Liquid dosage forms are prepared by dissolving the active agent and absorption enhancer in water. This liquid dosage form contains an effective amount of the pharmaceutically active agent dissolved therein. This liquid dosage form further comprises one or more fatty acid esters of sucrose as absorption enhancer having a combined HLB of about 8 to about 16; preferably about 9 to about 16 and more preferably about 9.5 to about 16. Conventional flavorants such as peppermint oil, natural and artificial flavorants, sugar or other natural and artificial sweeteners may be present in the same form of composition of this invention. These additives, flavoring agents, plasticizers and adjuvants may be incorporated into the liquid dosage form by adding to or mixing them into the aqueous solution. Small amounts of alcohol may be helpful in achieving solution of these components. Generally it is desired that these agents are present in the amount of from about 0.1% to about 20%. Flavorant is defined as a substance that gives another substance flavor, altering the characteristics of the solute, causing it to become sweet, sour, tangy, etc. There are three principal types of flavorings used in foods and useful in this invention, under definitions agreed in the E.U. and Australia:

Natural flavouring substances: Flavouring substances obtained from plant or animal raw materials, by physical, microbiological or enzymatic processes. They can be either used in their natural state or processed for human consumption, but cannot contain any nature-identical or artificial flavouring substances.

Nature-identical flavouring substances: Flavouring substances that are obtained by synthesis or isolated through chemical processes, which are chemically identical to flavouring substances naturally present in products intended for human consumption. They cannot contain any artificial flavouring substances.

Artificial flavouring substances: Flavouring substances not identified in a natural product intended for human consumption, whether or not the product is processed.

The following examples describe embodiments of the present invention is more detail.

Example 1

Preparation of 1 mg DES ODF

TABLE 2

Formula of Each ODF Strip (1 mg DES per 50 mg Film)

| Name | DES ODF | |
|---|---|---|
| Film Weight/Size | 2 cm × 2 cm | 50 |
| Dose in Diethylstilbestrol | | 1 |

| Ingredients | Dry Film mg | Dry Film w/w % |
|---|---|---|
| Diethylstilbestrol | 1.00 | 2.00% |
| Pullulan | 35.38 | 70.75% |
| Sucralose | 1.00 | 2.00% |
| PEG1500 | 2.50 | 5.00% |
| TiO₂ | 0.50 | 1.00% |
| Sorbitol | 1.50 | 3.00% |
| Alcohol | 0.00 | 0.00% |
| Glycerol | 5.00 | 10.00% |
| Sucrose Fatty Acid Esters D-1811 | 1.50 | 3.00% |
| Polysorbate 80 (Tween 80) | 0.75 | 1.50% |
| Sorbitan Monooleate (Span 80) | 0.13 | 0.25% |
| Cherry Flavor | 0.25 | 0.50% |
| Peppermint Oil | 0.13 | 0.25% |
| Spearmint oil | 0.13 | 0.25% |
| Menthol | 0.25 | 0.50% |
| Film Weight | 50.00 | 100.00% |

TABLE 3

Intermediate Formula
Intermediate Formula

| Ingedients | mg | % | 10 g |
|---|---|---|---|
| Alcohol | 5.00 | 36.76% | 3.68 |
| Glycerol | 5.00 | 36.76% | 3.68 |
| Sucrose Fatty Acid Esters D-1811 | 1.50 | 11.03% | 1.10 |
| Polysorbate 80 (Tween 80) | 0.75 | 5.51% | 0.55 |
| Sorbitan Monooleate (Span 80) | 0.13 | 0.92% | 0.09 |
| Cherry Flavor | 0.25 | 1.84% | 0.18 |
| Peppermint Oil | 0.13 | 0.92% | 0.09 |
| Spearmint oil | 0.13 | 0.92% | 0.09 |
| Menthol | 0.73 | 5.34% | 0.53 |
| Sum | 13.60 | 100% | 10 |

TABLE 4

Working Formula

| Ingredients | mg | % | 20 g |
|---|---|---|---|
| Diethylstilbestrol | 1.00 | 0.51% | 0.10 |
| 20% Pullulan Solution | 176.88 | 89.79% | 17.96 |
| Sucralose | 1.00 | 0.51% | 0.10 |
| PEG1500 | 2.50 | 1.27% | 0.25 |

TABLE 4-continued

| | Working Formula | | |
|---|---|---|---|
| Ingredients | mg | % | 20 g |
| TiO2 | 0.50 | 0.25% | 0.05 |
| Sorbitol | 1.50 | 0.76% | 0.15 |
| NAL1892INT | 13.60 | 6.91% | 1.38 |
| Sum | 196.98 | 100% | 20.0 |

Preparation Directions for Producing DES ODF
Stock Solutions
  1. Preparation of 20% Pullulan Solution (100 Gram)
  Dissolve 20 g of pullulan into 80 g of purified water, and mix well.
  2. Preparation of Intermediate Formula (10 Gram) (Refer to the Last Column of Table 3 for the Content of Each Ingredient)
  In a 20 ml glass vial, weigh and add sucrose fatty acid esters D1811, glycerin, alcohol, Tween 80, Span 80, Cherry flavor, Spearmint oil, Peppermint oil, and Menthol. Vortex for approximately 1 minute and bring the vial to a water bath at 60° C. in order to allow sucrose esters to dissolve.
  Preparation of Coating Solution (20 g of Working Formula, Refer to the last column of Table 4 for the content of each ingredient)
  1. In a glass beaker, add Diethylstilbestrol, then add 17.96 g of 20% pullulan stock solution, mix them well at 60° C.
  2. To the mixture, add $TiO_2$ and PEG1500. Mix them well at 60° C.
  3. To the mixture, add Sucralose and Sorbitol. Mix them well at 60° C.
  4. To the mixture, add 1.38 g of NAL1826INT intermediate stock solution. Mix them well at 60° C.
  5. After mixing, deaerate the above solution (Coating Solution) thoroughly.
Film Manufacture Directions
  1. Set up a sheet of PET release liner on a coating frame of the Mathis coater/dryer.
  2. Pour the deaerated Coating Solution carefully onto the PET release liner. Coat the film on the release liner by drawing down using a knife at the thickness of approximately 650-750 μm. Then dry the resulting film on the release liner at 80° C. for 25 minutes.
  3. Cut the dried film into strips each with a size of 2 cm by 2 cm. The target weight of each strip will be 50 mg which includes 1.0 gram of Diethylstilbestrol.

Pharmacokinetic Parameters

Protocol for the Study of the Comparative PK of Oral Solution and Oral Dissolving Film (ODF) Des in Sprague Dawley Rats All the studies were carried out in accordance with the Protocol for Animal Studies of the University of Houston. On arrival, the animals were allowed 7 days to acclimate to the animal room conditions before any manipulations.

The study design employed was parallel design. The animals were divided into two groups of A and B. Group A rats were dosed DES by oral gavage of suspension and group B rats were dosed ODF-DES through the buccal cavity. Blood samples were collected through a cannula in the jugular vein.

Procedures
  A) Preparation and Dosing of Oral Suspension of DES
  DES oral suspension was prepared at a concentration of 1 mg/ml by dispersing DES powder from capsules in Oral Suspending Vehicle (purchased from PCCA). The mixture was vortexed and sonicated so that the powder was uniformly dispersed. Each animal was then dosed by oral gavage 1 ml of the suspension under light anesthesia with ketamine/xylazine/acepromazine. Blood samples of 0.25 ml were collected at 0.5, 1, 2, 4, 8, 12, 24 and 30 h post dose in heparinized tubes, respectively. The blood samples were immediately centrifuged at 13,000 rpm and the clear supernatant (plasma) collected and stored at −80° C., until during analysis.
  B) Preparation and Dosing of ODF-DES
  Each ODF-DES film containing 1 mg of DES was cut into 2 pieces. Under the light anesthesia, both pieces were carefully inserted into the buccal cavity of the rats on each side. Blood samples were collected at 0.25, 0.5, 1, 2, 4, 8, 12, 24, and 30 h into a heparinized tubes. The samples were centrifuged and the plasma collected and stored under −80° C.
  C) Preparation of Samples and Analysis
  DES was extracted from the plasma samples using ethyl acetate at a ratio of 1:5. One hundred micro-liter of plasma was transferred into a vial and 500 μl of ethyl acetate and 10 μl of 5 μM daidazein (internal standard) were added. The mixture was vortexed and centrifuged and the clear supernatant was air-dried and reconstituted with 100 μL of 50% acetonitrile. The reconstituted mixture was analyzed using a validated LC-MS/MS assay.
  D) Data Analysis
  The data was analyzed using WinNonlin software.
Dosing of Oral Suspension
  DES oral suspension was prepared at a concentration of 1 mg/ml by dispersing DES powder from capsules in Oral Suspending Vehicle (purchased from PCCA). Any commercially available suspending vehicle may be used. Formulas may be found in the *USP Pharmacist's Pharmacopeia* 2005: 218, 347, 376, 408-413 and in the 2006 *United States Pharmacopeia* (*USP*) 29—*National Frmulary* 24, 2006: 1395, 2731-2735, 3263, 3456. The mixture was vortexed and sonicated so that no powder particles were visible. Each animal (n=4) was then dosed by oral gavage 1 ml of the suspension under light anesthesia with ketamine/xylazine/acepromazine. Blood samples of 0.25 ml were collected by the tail vein at 0.5, 1, 2, 4, 8, 12, 24 and 30 h post dose in heparinized tubes, respectively. The blood samples were immediately centrifuged at 13,000 rpm and the clear supernatant (plasma) collected and stored at −80° C., until during analysis.
Experimental Design
  Plasma levels of DES and fibrinogen were determined using a validated LC/MS-MS bio-analytical method.
  The assay for DES in plasma was developed using an LC-MS/MS instrument. Ethyl acetate was used as the extraction solvent and daidzein, an isoflavone, was the internal standard. The linearity of the assay was established in the range of 0.39-100 ng/ml. The accuracy and precision of the say was determined using quality control samples (n=6 each). The assay validation was carried out according to the FDA Guidance's for Bioanalytical Method Validation.
Equipment
  The assay was developed with an AP 3200 Qtrap triple quadruple mass spectrometer. The main MS/MS parameters were set as follows: curtain gas, nitrogen, psi; gas 1, nitrogen, 80 psi; gas 2, nitrogen, 40 psi; ion source temperature, 500° C.; ion spray source voltage, −4500 kv. The transitions for DES and internal standard monitored are m/z 266.9-m/z 237.3 and m/z 253.0-m/z 132.0, respectively. The LC is an Agilent Technologies 1200 series and the separation was done using an Agilent Eclipse XDB-C18 column (5μ, 4.6× 150 mm), maintained at a temperature of 40° C. The gradient mobile phases were: 2.5 mM ammonium acetate, PH 70.6 (A) and 100% acetonitrile (B), with 35% B (0-1 min), 35-95% B (1-5 min), 95% B (5-6 min), and 35% B (7-8 min). The flow rate and injection volume were 1 ml/min and 50 μL, respectively.

Chemicals and Reagents

The DES used was of purity greater than 99%. All other reagents were of analytical great. Deionized water was obtained in house using the Milli-Q UV Plus purifying system. Blank plasma was kindly donated by the Methodist Hospital at the Texas Medical Center in Houston, Tex.

Stock Solutions and Standards

A stock solution of DES at 1 mg/ml in MeOH was prepared and store at −20° C. The stock solution was diluted to 10 μg/ml using 50% acetonitrile and further diluted with plasma to 100 ng/ml working solution. Serial dilutions were made from the working solution to prepare the calibration standards and quality control (QC) samples. Stock solution of Daidzein at 10 mM prepared in DMSO/MeOH 25/75 was diluted with DMSO/MeOH to 100 μM then with 50% acetonitrile to a working solution of 50 μM. The working solution of DES was stored at −80° C., while the working solution daidzein was stored at −20° C.

The levels of fibrinogen were analyzed using the Assay-Max Rat Fibrinogen (FBG) ELISA Kit for plasma samples. This kit comes with protocol instructions. Any equivalent assay kit may be employed. We employed the same protocol and the plasma samples were diluted with the mix diluent twice to a final dilution of 1:2000. Briefly, 1) All reagents were to room temperature before use. The assay was performed at room temperature (20-300 C).

2) Add 25 μl of standard or sample per well and immediately added 25 μl of Biotinylated FBG to each well (on top of the Standard or sample). The wells were covered with a sealing tape and incubated for two hours. Timer was started after the last sample addition.

3) Each well was washed five times with 200 μl of Wash Buffer (provided). The plate was inverted to decant the contents, and hit 4-5 times on absorbent paper towel to complete remove liquid at each step.

4) Fifty microliter of Streptavidin-Peroxidase Conjugate (also provided) was added to each well and incubated for 30 minutes.

5) The wells were washed again five times with 200 μl of Wash Buffer as above.

6) Fifty microliter of Chromogen Substrate (provided) was added per well and incubated for about 10 minutes or till the optimal color density develops 7) Add 50 μl of Stop Solution (provided) to each well. The color changed from blue to yellow.

8) The absorbance was read on a microplate reader at a wavelength of 450 nm immediately.

Data Analysis

The mean value of the triplicate readings for each standard and sample were calculated.

A Standard Curve was generated using a plot 4-parameter graph using the standard concentrations on the x-axis and the corresponding mean 450 nm absorbance on the y-axis. The best-fit line was determined by regression analysis using log-log or four-parameter logistic curve-fit.

Determined the unknown sample concentration from the Standard Curve and multiply the value by the dilution factor.

Results:
For Tables 5 to 8,
C1, C2, C3, C4 represent plasma concentrations from different animals. All of the animals were Sprague-Dawley rats.
ODF is the film dosage form
DES is diethylstilbestrol
FBN is fibrinogen
Time is measured in hours
Concentration is measured in nanograms per milliliter (ng/ml)

TABLE 5

Plasma levels in ng/ml of DES versus time post administration of the ODF

| time(h) | ODF-DES CONCENTRATION (ng/ml) | | | | | |
|---|---|---|---|---|---|---|
| | C1 | C2 | C3 | C4 | mean | std |
| 0.25 | 7.18 | 5.26 | 7.02 | 5.15 | 6.15 | 1.10 |
| 0.5 | 0.15 | 1.72 | 0.47 | 2.23 | 1.14 | 0.99 |
| 1 | 5.54 | 4.05 | 3.67 | 1.00 | 3.57 | 1.89 |
| 2 | 10.25 | 5.55 | 5.51 | 25.34 | 11.66 | 9.39 |
| 4 | 9.52 | 11.52 | 9.08 | 21.56 | 12.92 | 5.86 |
| 8 | 6.73 | 4.05 | 7.59 | 9.11 | 6.87 | 2.12 |
| 12 | 4.55 | 3.75 | 6.12 | 3.17 | 4.40 | 1.28 |
| 24 | 4.20 | 3.97 | 3.45 | 1.68 | 3.32 | 1.14 |
| 30 | 0.87 | 3.69 | 3.34 | 3.33 | 2.81 | 1.30 |

Table 5 contains the concentration in plasma for DES for up to 30 hours post administration of the ODF containing 1 mg of DES.

TABLE 6

Plasma levels in ng/ml of FBN versus time post administration

| time(h) | C1 | C2 | C3 | C4 | MEAN | STD |
|---|---|---|---|---|---|---|
| 0.25 | 3.88 | 1.41 | 4.65 | 4.87 | 3.70 | 1.58 |
| 0.5 | 1.60 | 0.53 | 1.24 | 0.87 | 1.06 | 0.46 |
| 1 | 1.23 | 1.19 | 0.47 | 1.17 | 1.01 | 0.36 |
| 2 | 2.39 | 3.06 | 1.55 | 1.71 | 2.18 | 0.69 |
| 4 | 4.02 | 1.49 | 3.48 | 4.71 | 3.42 | 1.39 |
| 8 | 3.42 | 1.53 | 2.22 | 6.35 | 3.38 | 2.13 |
| 12 | 2.88 | 3.21 | 2.57 | 5.98 | 3.66 | 1.57 |
| 24 | 4.35 | 3.93 | 4.01 | 4.78 | 4.27 | 0.39 |
| 30 | 2.59 | 1.89 | 1.72 | 4.26 | 2.62 | 1.16 |

Table 6 contains the concentration in plasma for FBN for up to 30 hours post administration of the ODF containing 1 mg of DES.

TABLE 7

Plasma levels in ng/ml of DES versus time post administration of the oral suspension

| time(h) | conc(ng/ml) | | | | | |
|---|---|---|---|---|---|---|
| | C1 | C2 | C3 | C4 | mean | std |
| 0.5 | 2.68 | 5.10 | 0.15 | 3.85 | 2.95 | 2.11 |
| 1 | 12.87 | 16.72 | 2.48 | 11.52 | 10.90 | 6.02 |
| 2 | 3.67 | 8.42 | 1.59 | 4.81 | 4.62 | 2.86 |
| 4 | 2.65 | 5.70 | 0.66 | 3.85 | 3.22 | 2.12 |
| 8 | 2.34 | 1.96 | 0.40 | 0.53 | 1.31 | 0.98 |
| 12 | 2.30 | 0.89 | 0.00 | 0.33 | 0.88 | 1.00 |
| 24 | 2.12 | 0.41 | 0.00 | 0.30 | 0.71 | 0.96 |
| 30 | 1.96 | 0.43 | 0.00 | 0.21 | 0.65 | 0.89 |

Table 7 contains the concentration in plasma for DES for up to 30 hours post administration of the oral suspension containing 1 mg of DES.

TABLE 8

Plasma levels in ng/ml of FBN versus time
post administration of the Oral Suspension

| time(h) | C1 | C2 | C3 | C4 | MEAN | STD |
|---|---|---|---|---|---|---|
| 0.5 | 2.47 | 2.24 | 1.98 | 1.81 | 2.12 | 0.29 |
| 1 | 1.49 | 2.05 | 1.24 | 2.01 | 1.70 | 0.40 |
| 2 | 3.13 | 1.75 | 0.64 | 0.73 | 1.56 | 1.16 |
| 4 | 2.42 | 3.26 | 3.09 | 2.33 | 2.78 | 0.47 |
| 8 | 2.26 | 4.25 | 3.65 | 2.87 | 3.26 | 0.87 |
| 12 | 2.27 | 2.41 | 3.90 | 3.61 | 3.05 | 0.83 |
| 24 | 1.65 | 1.28 | 2.29 | 1.70 | 1.73 | 0.42 |
| 30 | 1.40 | 2.11 | 2.52 | 2.66 | 2.17 | 0.57 |

Table 8 contains the concentration in plasma for FBN for up to 30 hours post administration of the oral suspension containing 1 mg of DES.

Figure 2:
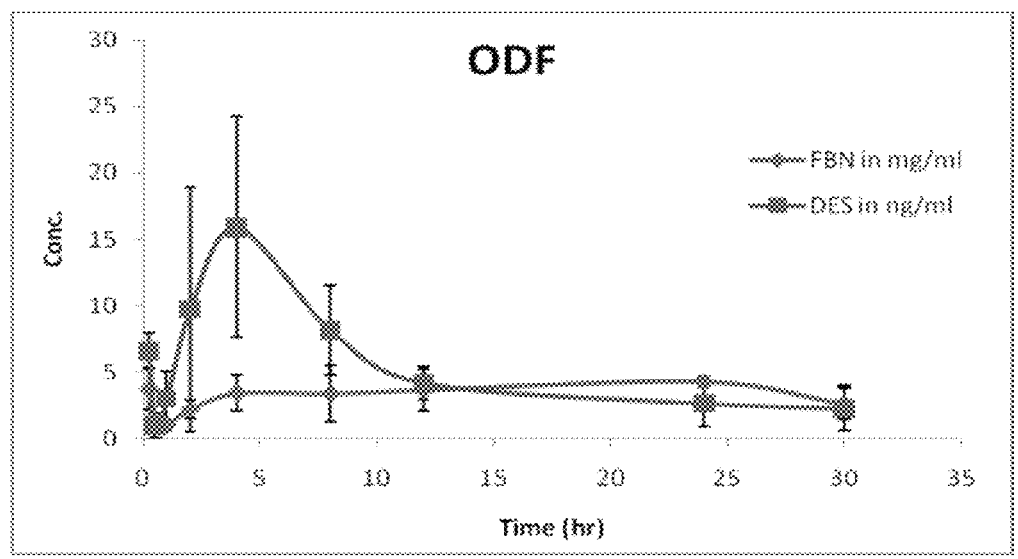
FIG. 2 is a graph of plasma concentrations of FBN and DES from Sprague-Dawley rats dosed with ODF-DES (n=4).
Figure 3:
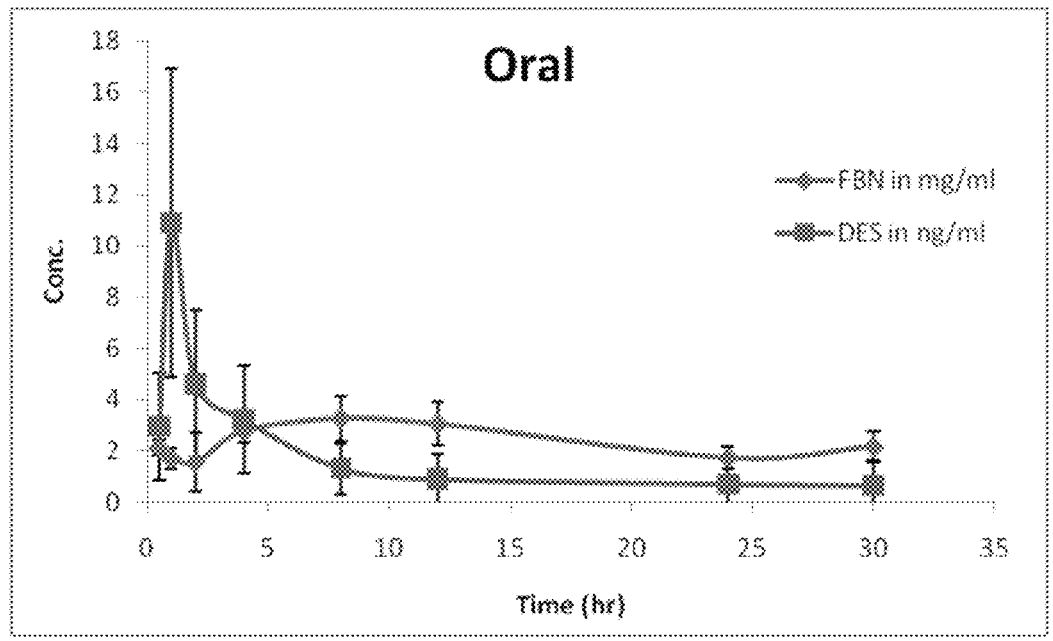
FIG. 3 is a graph of plasma concentrations of FBN and DES from Sprague-Dawley rats dosed with oral solution of DES (n=4).
Figure 4:
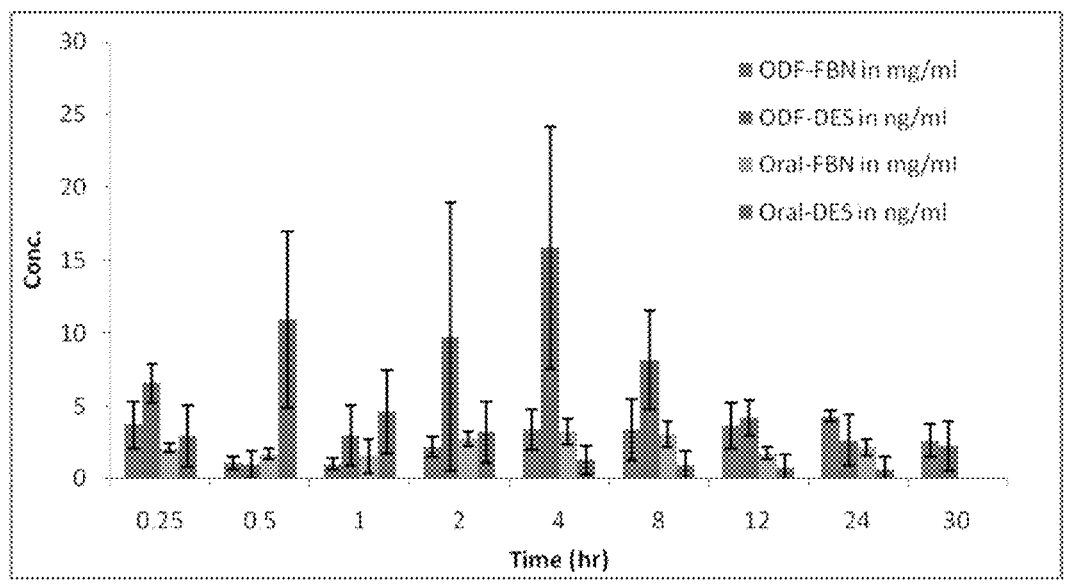
FIG. 4 is a graph of plasma concentrations of FBN and DES from Sprague-Dawley rats dosed with ODF and oral solution of DES (n=4).

The effectiveness of the present invention is illustrated in tables 5-8 and FIGS. 1-6. FIGS. 1-6 are graphical representations of the mean plasma level data contained in tables 3-6. FIGS. 1 and 4 illustrates the high plasma level of DES obtained from the ODF dosage form compared to the oral suspension of the same amount, 1 mg, of DES. Tables 5 and 7 contain the numerical data. FIGS. 1 and 4 also illustrate that the amount of fibrinogen produced by the ODF dosage form and the oral suspension is about the same. These data illustrate that the ODF dosage form produces much higher plasma levels without the risk of increased side effects from the production of fibrinogen.

FIGS. 2 and 3 illustrate the relative relationship of DES plasma levels versus fibrinogen plasma levels for the ODF and oral suspension dosage form respectively.

Figure 5:
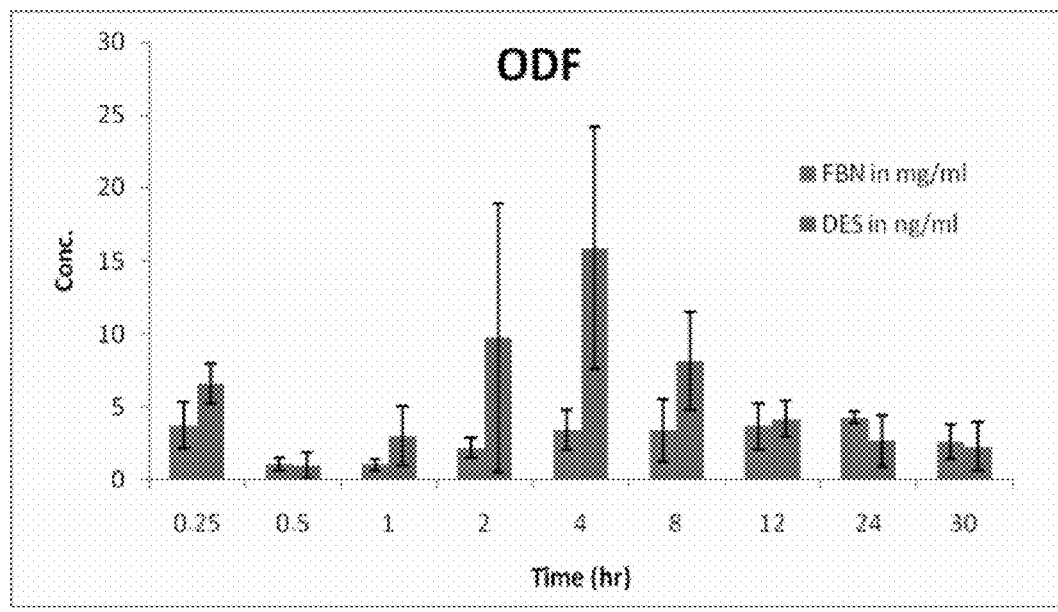
FIG. 5 is a graph of plasma concentrations of FBN and DES from Sprague-Dawley rats dosed with ODF-DES (n=4).
Figure 6:
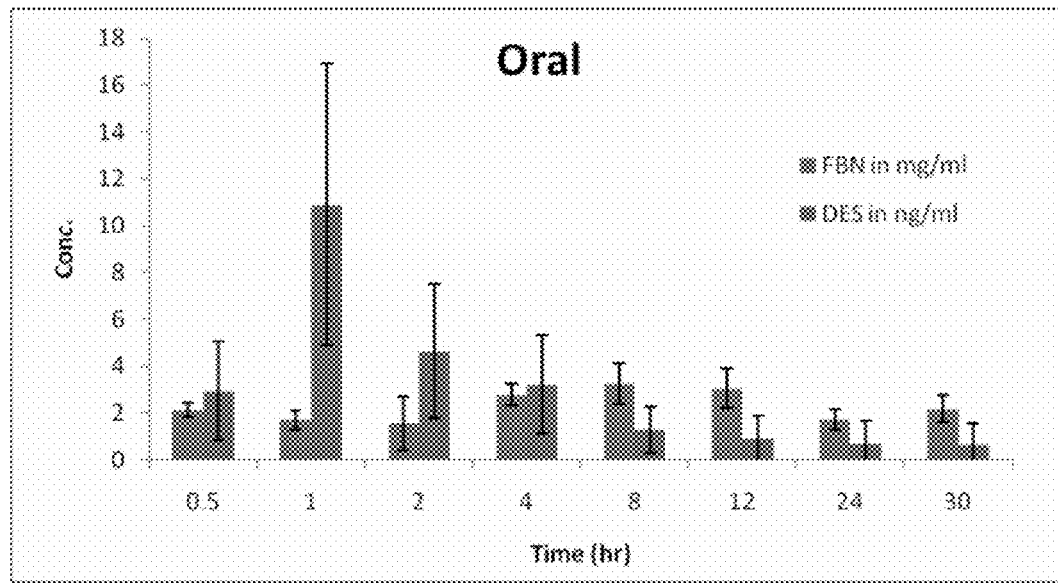
FIG. 6 is a graph of plasma concentrations of FBN and DES from Sprague-Dawley rats dosed with oral solution of DES (n=4).

FIGS. 5 and 6 illustrate in bar graph format the data contained in tables. These FIGS. 5 and 6 along with FIG. 5 plot the mean for each time period as well as indicating the range of results for the animals at each time period. In FIGS. 5 and 6, the bar on the left for each time period represents fibrinogen content and the bar on the right for each time period represents DES content.

For FIG. 4, the bar on the left for each time period represents fibrinogen content for the ODF dosage form and the second bar from the left represents DES content from the ODF dosage form. The third bar from the left for each time period represents fibrinogen content for the oral suspension dosage form and the fourth bar from the left represents the DES content for the oral suspension dosage form.

Although the description above contains much specificity, these should not be construed as limiting the scope of the invention but as merely providing illustrations of some of the presently preferred embodiments of this invention. Various other embodiments and ramifications are possible within it's scope. For example, instead of the direct prostatic implants of androgen suppressive natural and synthetic steroidal and related chemical hormonal formulations, they may be implanted as subcutaneous or intramuscular implants for the treatment of prostate cancer especially as primary hormonal treatment of favorable prognostic early stage prostate cancer as alternative treatment by surgery or radiation therapy and for the treatment of hormone refractory advanced prostate cancer.

Thus the scope of the invention should be determined by the appended claims and their legal equivalents, rather than by the examples given.

What is claimed:

1. A method for treating prostate or breast cancer in a patient comprising
administering the oral unit dosage form as a water soluble matrix to the oral mucosal membranes of the mouth of a patient, which matrix contains, dispersed therein, a pharmaceutical agent selected from the group consisting of diethylstilbestrol and pharmaceutically acceptable salts of diethylstilbestrol, said pharmaceutical agent being present in said matrix in an amount effective for treating said prostate or breast cancer, said matrix composed of a one or more sucrose fatty acid esters having an HLB of about 8 to 16, wherein the matrix is a film whereby the pharmaceutical agent is absorbed through the mucosal membrane providing high blood levels of diethylstilbestrol and low levels of fibrinogen.

2. The method of claim 1, further comprising a polymeric mixture of polyvinyl pyrrolidone and a polymeric alginate.

3. The method of claim 2, wherein the ratio of polyvinyl pyrrolidone to polymeric alginate in the polymeric mixture is from about 5:1 to about 1:3.

4. The method of claim 2, wherein the polymeric mixture contains, from about 5% to about 95% by weight of polyvinyl pyrrolidone and from about 5% to about 95% by weight of an polymeric alginate, both of said weights being based on the weight of said polymeric mixture.

5. The method of claim 1, wherein the diethylstilbestrol and pharmaceutically acceptable salts of diethylstilbestrol is present in an amount of about 0.1 to about 5 mg.

6. The method of claim 1, wherein said matrix is placed under the tongue of said patient.

7. The method of claim 1, wherein said matrix is inserted on the buccal tissue of the mouth of the patient.

8. The method of claim 1, wherein the sucrose fatty acid ester has a monomer content of from about 20 percent to about 80 percent.

9. The method of claim 1, wherein the sucrose fatty acid esters are selected from the group consisting of sucrose stearate, sucrose palmitate, sucrose laurate, sucrose behenate, sucrose oleate and sucrose erucate.

10. The method of claim 1, wherein said absorption enhancer is present in an amount of from about 1% to about 20% based upon the weight of the film.

11. The method of claim 1, further comprising a nonionic surfactant wherein the combined nonionic surfactant and sucrose fatty acid ester have a combined HLB of about 8 to about 17.

12. The method of claim 1, further comprising a secondary absorption enhancer selected from the group consisting of glycerol, tween, span, ginger oil, cineole and terpenes.

13. The method of claim 1, further comprising pullulan as a film forming agent.

14. The method of claim 1, wherein the active agent is released over a period of time from about 0.25 minutes to about 15 minutes.

15. The method of claim 1, wherein the active agent is released over a period of time from about 0.5 minutes to about 10 minutes.

16. The pharmaceutical composition of claim 1, further comprising a film forming agent selected from pullulan or a polymeric mixture of polyvinyl pyrrolidone and a polymeric alginate.

17. The pharmaceutical composition of claim 1, further comprising a film forming agent selected from pullulan.

* * * * *